United States Patent
Vaillant et al.

(10) Patent No.: US 9,138,197 B2
(45) Date of Patent: Sep. 22, 2015

(54) SELECTION OF OPTIMAL VIEWING ANGLE TO OPTIMIZE ANATOMY VISIBILITY AND PATIENT SKIN DOSE

(75) Inventors: Regis Vaillant, Buc (FR); Lionel Desponds, Buc (FR); Vincent Bismuth, Buc (FR); Pal Tegzes, Budaors (HU); Gabor Simon, Budaors (HU); Tamas Ujvari, Budaors (HU); Zsolt Szabo, Budaors (HU); Gyorgy Szekely, Budaors (HU)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 0 days.

(21) Appl. No.: 13/324,311

(22) Filed: Dec. 13, 2011

(65) Prior Publication Data

US 2012/0150520 A1 Jun. 14, 2012

(30) Foreign Application Priority Data

Dec. 14, 2010 (EP) .................................... 10306410

(51) Int. Cl.
  *G01N 33/48* (2006.01)
  *G01N 31/00* (2006.01)
  *G06G 7/48* (2006.01)
  (Continued)

(52) U.S. Cl.
  CPC ............... *A61B 6/4441* (2013.01); *A61B 6/463* (2013.01); *A61B 6/466* (2013.01); *A61B 6/504* (2013.01); *A61B 6/542* (2013.01); *G06F 17/30* (2013.01);
  (Continued)

(58) Field of Classification Search
  CPC ......... G06F 19/12; G06F 19/26; G06F 19/28; G06T 17/30
  See application file for complete search history.

(56) References Cited

U.S. PATENT DOCUMENTS 6,404,843 B1 * 6/2002 Vaillant .............................. 378/8
6,424,731 B1 * 7/2002 Launay et al. ................. 382/128
(Continued)

FOREIGN PATENT DOCUMENTS

CN 1636512 A 7/2005
CN 1736333 A 2/2006
(Continued)

OTHER PUBLICATIONS

Auricchio et al. Accuracy and usefulness of fusion imaging between three-dimensional coronary sinus and coronary veins computed tomographic images with projectiom images obtained using fluoroscopy. Eurospace, 2009, vol. 11, pp. 1483-1490.*

(Continued)

*Primary Examiner* — Russell S Negin
(74) *Attorney, Agent, or Firm* — GE Global Patent Operation; Marc A. Vivenzio (57) ABSTRACT

A method is provided for monitoring the radiation dose in a body to be imaged using an X-ray imaging device comprising an X-ray emitting source, a detector, a processing unit and a display. The method comprises exposing the body to be imaged to radiation doses to acquire initial 2D images; computing a 3D model of the body in relation to the initial 2D images using the processing unit; applying a model of the interactions between matter and radiation to the 3D model of the body using the processing unit; calculating, using the processing unit, a dose map of the distribution of the accumulated radiation dose in the 3D model for parameters that define the conditions of X-ray exposure; and displaying the 3D model of the body oriented according to the position of the emitting source with the dose map.

9 Claims, 3 Drawing Sheets

(51) Int. Cl.
　　*G06F 17/50*　　(2006.01)
　　*A61B 6/00*　　(2006.01)
　　*G06F 17/30*　　(2006.01)
　　*G06F 19/28*　　(2011.01)
　　*G06F 19/26*　　(2011.01)
　　*G06F 19/12*　　(2011.01)

(52) U.S. Cl.
　　CPC ............... *G06F 19/12* (2013.01); *G06F 19/26* (2013.01); *G06F 19/28* (2013.01)

(56) References Cited

U.S. PATENT DOCUMENTS

| 7,072,437 | B2 | 7/2006 | Seto |
| 7,082,183 | B2 | 7/2006 | Toth et al. |
| 7,995,819 | B2 * | 8/2011 | Vaillant et al. ............... 382/128 |
| 2008/0144903 | A1 | 6/2008 | Wang et al. |
| 2008/0144908 | A1 | 6/2008 | West et al. |
| 2009/0005668 | A1 | 1/2009 | West et al. |

FOREIGN PATENT DOCUMENTS

| DE | 102008047811 A1 | 4/2010 |
| EP | 1393681 A1 | 3/2004 |
| JP | 2010269165 A | 12/2010 |
| WO | 2007080522 A1 | 7/2007 |
| WO | 2008061565 A1 | 5/2008 |

OTHER PUBLICATIONS

European Search Report for EP application No. 10306410.1 issued Mar. 22, 2011, pp. 1-5.

1a/ ThoraxCenter Rotterdam:? A den Boer, P J de Feijter, P W Serruys and J R T C Roelandt, Real-Time Quantification and Display of Skin Radiation During Coronary Angiography and Intervention Circulation (2001) 104:1779-1784.

1b/ Caregraph accuracy: LT Muhammed A. Ozeroglu,?title of Thesis: Verification of Caregraph? Peak Skin Dose Data Using Radiochromic Film? (Jun. 2005)? Uniformed Services University of the Health Sciences, Bethesda MD, USA.

2/ NY University Buffalo: K Chugh , P Dinu, D R Bednarek, D Wobschall, S Rudin, K Hoffmann, R Peterson and M Zeng, A Computer-Graphic Display for Real-Time Operator Feedback During Interventional X-Ray Procedures. Proceedings of SPIE (2004) 5367:464-473.

3/ San Giovanni Battista Hospital: O Rampado and R Ropolo, A method for a real time estimation of entrance skin dose distribution in interventional neuroradiology Med. Phys. (2004) 31, 2356?2361.

4/ University of Nottingham: R E Morrell, title of Thesis: Dosimetry and Optimisation in High Dose Fluoroscopic and Fluorographic Procedures (Mar. 2006) Universiy of Nottingham, UK.

Unofficial English translation of Chinese Office Action and Search Report issued in connection with corresponding CN Application No. 201110463086.8 on Sep. 19, 2014.

Guimarães, Carla C. et al., "Performance of GEANT4 in dosimetry applications: Calculation of X-ray spectra and kerma-to-dose equivalent conversion coefficients", Radiation Measurements, 2008, vol. 43, Issues 9-10, pp. 1525-1531.

Finet, G. et al., "Optimizing coronary angiographic views", International Journal of Cardiac Imaging, 1995, vol. 11, Issue 1, pp. 53-54.

Dworzak, Jalda et al, "3D reconstruction of the human rib cage from 2D projection images using a statistical shape model", International Journal of Computer Assisted Radiology and Surgery, Mar. 2010, vol. 5, Issue 2, pp. 111-124.

* cited by examiner

SELECTION OF OPTIMAL VIEWING ANGLE TO OPTIMIZE ANATOMY VISIBILITY AND PATIENT SKIN DOSE

BACKGROUND OF THE INVENTION

1. Field of the Invention

The field of the invention relates to the area of medical imaging by radiation. In particular, it concerns the estimation monitoring and display of radiation doses to which a body or certain organs thereof are subjected when acquiring images.

2. Description of Related Art

The highest risk of skin injury occurs in case of long and difficult interventional procedures.

These procedures often involve the acquisition of a 3D volume of the diseased body part, or the usage of pre-acquired (typically via CT or MR) 3D information of the treated anatomy. This 3D volume is reconstructed and stored on a review station connected to the vascular x-ray system, and means are provided to display the 3D information in the exam room on a separate monitor. Several features are already available using this module. The "send angle" feature allows to find an optimal viewing angle by rotating the 3D model, and then automatically send the gantry to the selected angle.

In the "Follow the gantry" mode the 3D model is automatically rotated based on the gantry motions so that the viewing angle corresponds to the current gantry positions.

The features described above allow the optimization of the geometry of the imaging systems used in the intervention based on the properties of the treated anatomy. However no information is provided that would enable the user to take the potential adverse impact of radiation into account in the optimization method.

There is therefore a need for a tool enabling the user to estimate the distribution of the radiation doses received by a body or by different parts of a body during the acquisition of one or more radiological images.

It is also desired, during the acquisition of new images, to avoid accumulating radiation doses that are too high in some regions of the body or in some organs, and consequently to be able to define the conditions of acquisition for subsequent images allowing optimization of the radiation doses accumulated in a body.

Methods are already known allowing an estimate of the distribution of the radiation doses accumulated by a body. However, the known methods do not provide the user with appropriate information that enable him to perform an effective determination of the optimized acquisition conditions of X-rays.

Besides, there is a need for an improved model of the skin of a subject, or more generally the surface of the body to be imaged, in order to obtain an accurate dose map.

BRIEF SUMMARY OF THE INVENTION

One embodiment of the present invention provides a method for monitoring the radiation dose in a body to be imaged using an X-ray imaging device comprising an X-ray emitting source, a detector, a processing unit and a display. The method comprises exposing the body to be imaged to radiation doses to acquire initial 2D images; computing a 3D model of the body in relation to the initial 2D images using the processing unit; applying a model of the interactions between matter and radiation to the 3D model of the body using the processing unit; calculating, using the processing unit, a dose map of the distribution of the accumulated radiation dose in the 3D model for parameters that define the conditions of X-ray exposure; and displaying the 3D model of the body oriented according to the position of the emitting source with the dose map.

According to another embodiment of the present invention, a medical imaging device is provided. The medical imaging device comprises an X-ray emitting source and a detector positioned facing the X-ray emitting source, wherein the body to be imaged is exposed to radiation doses from the X-ray emitting source to acquire initial 2D images. The medical imaging device further comprises a processing unit configured to: compute a 3D model of the body in relation to the initial 2D images; apply a model of the interactions between matter and radiation to the 3D model of the body; and calculate a dose map of the distribution of the accumulated radiation dose in the 3D model for parameters that define the conditions of X-ray exposure. The medical imaging device comprises a display on which the 3D model of the body oriented according to the position of the emitting source with the dose map is displayed.

BRIEF DESCRIPTION OF SEVERAL VIEWS OF THE DRAWINGS

Other characteristics, purposes and advantages of embodiments of the invention will become apparent from the following description, which is solely illustrative and is non-limiting, and is to be read in connection with the appended drawings in which.

DETAILED DESCRIPTION OF THE INVENTION

Figure 1:
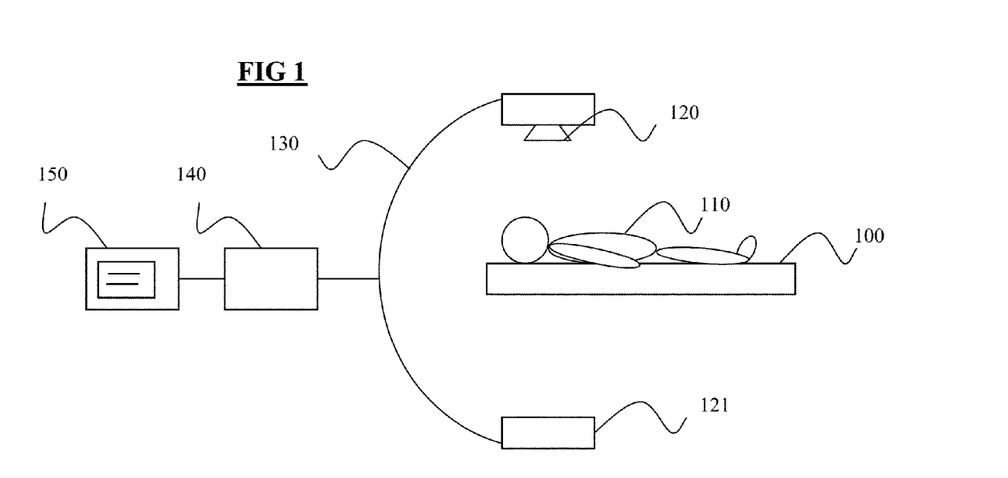
FIG. 1 is a schematic illustration of an imaging device in accordance with an embodiment of the present invention.

FIG. 1 schematically illustrates a C-arm medical imaging device. The medical imaging device comprises a table 100 on which the subject 110 is positioned, an emission source 120 (e.g. X-ray source) arranged at one end of a C-arm 130, and a detector 121—for example an array of digital sensors—positioned facing the emission source 120, on the other side of the table 100 and subject 110, and carried by the other end of the C-arm 130.

The C-arm 130 is mobile relative to the table 100. It can be tilted to allow different exposure angles. It can also be moved longitudinally along the table.

In other embodiments, or to supplement the mobility of the C-arm 130, the table 100 is mobile to offer greater flexibility in the different movements.

The device also comprises a processing unit such as a computer 140 or set of computers, receiving the images acquired by the detector 121 and programmed to process these images and perform the steps described below with reference to FIGS. 2 to 4.

This computer can additionally be combined with a display 150 such as a screen to display the result of this method.

Figure 2:
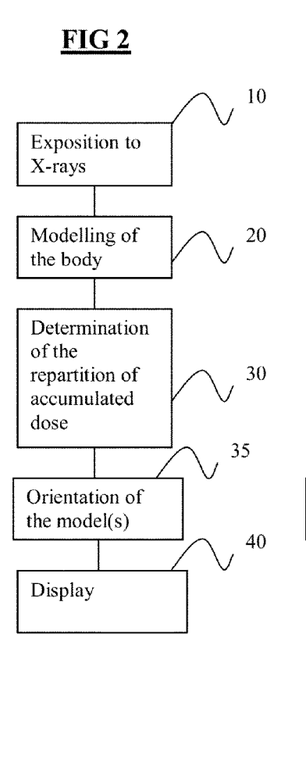
FIG. 2 illustrates the steps of an example of a method conforming to an embodiment of the invention, able to be implemented with the device in FIG. 1.

In FIG. 2, at a first step 10, the body 110 or part thereof, is exposed to a few radiation doses during the acquisition of initial 2D images around a patient undergoing an imaging process implementing the method according to an embodiment of the invention.

At a second step 20, in relation to these 2D images, the computer 140 computes a 3D modelling of the subject of the part thereof which has been the subject of these acquisitions of images, and processes this 3D modelling to produce a 3D model in which different elements of the body or part of the body of which images have been acquired can be identified.

The processing applied uses segmenting and reconstruction techniques known per se. It also identifies, in the 3D model, different elements or organs of the body of the patient (bone, flesh, heart, liver, lungs for example).

The 3D model thus produced therefore takes into account the variations in density of the different elements forming the body of the subject, and is not limited to modelling reduced to a simple geometric shape having homogeneous density Said 3D model can be obtained for example in the manner described in the article "3D reconstruction of the human rib cage from 2D projection images using a statistical shape model; Jalda Dworzak et al. Int J Cars (2010) 5:111-124".

In particular, with the technique such as proposed in this publication, the patient's body is reconstructed in 3D avoiding a rotational acquisition if such rotation requires an X-ray dose in addition to the standard examination, and for this purpose the images are used that are naturally acquired during the examination.

For example, in interventional cardiology, 2D images are acquired over a certain set of angles around the patient's body during the diagnosis phase. These images, in a restricted number of views, are processed by the computer 140 which reconstructs the anatomic structures for which statistical shape models are available for example.

In an alternative embodiment of the invention, the 3D model can be obtained from previous acquisitions, or can be a standardized model such as a cylinder, a sphere or any adapted geometrical volume.

At a calculation step 30, to the 3D model thus obtained, the computer 140 applies a previously memorized model of the interactions between matter and radiation, for instance a theoretical model, which defines a theoretical model of radiation absorption and diffusion in the patient's body. In relation to this 3D model, to this theoretical model and to a certain number of additional data on the conditions of image acquisition, it computes a dose map corresponding to the distribution of the doses of radiations accumulated in the different parts of the patient. Said theoretical model, for example, is of the type described in the numerous recent studies using Geant4 software to model and simulate the interaction of photons with matter, e.g.: "Performance of GEANT4 in dosimetry applications: Calculation of X-ray spectra and kerma-to-dose equivalent conversion coefficients; Carla C. Guimaraes, Mauricio Moralles, Emico Okuno; Radiation Measurements 43 (2008) 1525-1531".

The parameters that are taken into account and applied to this model are for example: the emission characteristics (voltage in kV, intensity in mA); the properties of the emission tube; the focal spot size of emission; the properties of the body of the subject under consideration, notably the densities and different properties of the different organs of the subject's skeleton.

It will be noted here that this step does not require any additional measurement instruments, which means that it is possible to continue to use a device for the implementation of this method with a structure substantially similar to the structure of a conventional imaging device, with the exception of the computer that is adapted to perform the specific operations.

Several levels of precision can be obtained, for example by only taking into account absorbed radiation, or also taking X-ray diffusion into account.

In a display step 40, the computer 140 commands the display of the dose map or 3D mapping of the accumulated doses thus obtained, typically by presenting a 3D image with graded colours corresponding to different levels of accumulated radiation doses.

The accumulated dose can be displayed only for the surface of the 3D model, therefore corresponding to the dose delivered to the skin of the body.

The 3D model is displayed together with the dose map, both being oriented according to the current position of the emission source 120.

This orientation of the 3D model and the dose map can be achieved in an orientation step 35 which typically occurs between the steps 30 and 40 as illustrated on FIG. 2.

In this orientation step 35, the computer 140 applies a previously memorized algorithm which processes the 3D model and the dose map along with information regarding the positioning of the emitting source 120 in order to define the appropriate orientation of the 3D model and the dose map that are displayed in step 40.

This determination of the distribution of an X-ray dose in the body of a subject can be given several uses.

It can be used for example, subsequent to exposure of the subject, to verify that this exposure has been safely conducted for the subject, by not excessively exposing certain parts of the subject's body.

It can also be used to determine the best directions of exposure to be used for subsequent exposures, so as not to expose some parts of the subject's body to an excessive radiation dose. This method provides the user with an improved anatomy and skin dose visibility that enables the user to perform a trade-off between the exposition of the body to radiations, and the interest of the angulations for anatomy assessment.

The dose map and the 3D model of the body 110 can be updated on each new acquired 2D image. The distribution of accumulated dose can then optionally be recalculated.

As it will have been understood, the case has been taken here in which the images processed to determine the 3D model of the body 110, and notably the first 3D model, are 2D images acquired during an interventional procedure.

Evidently, as a variant for the processing of modelling and to identify different elements or organs of a patient's body, it is also possible to envisage the use of a 3D image acquired prior to the procedure, for example CT or MRI.

Processing to adjust subsequently acquired images to the initial 3D model can then be used to obtain a more accurate 3D model.

Figure 3:
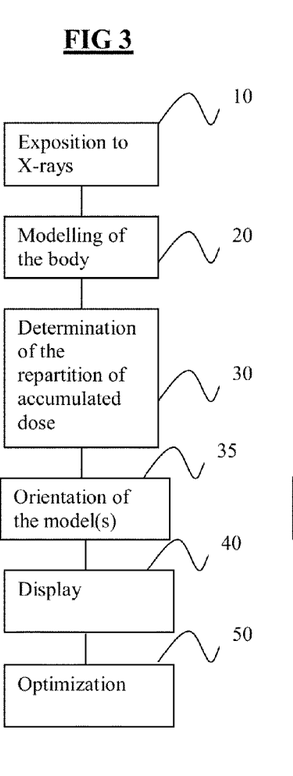
FIGS. 3 and 4 illustrate two other possible embodiments of the present invention.

Also, as illustrated by the embodiment shown in FIG. 3, it is possible to make provision for an additional optimization step 50, which consists in determining the best adapted directions of exposure so as not to expose some regions of the subject's body to an X-ray dose that is too high.

Similar to the calculation step 30 described previously, the optimization step 50 takes numerous parameters in account of which mention may be made of the following: the characteristics of the X-rays it is desired to emit; the properties of the X-ray emission tube; the focal spot size of emission; the properties of the subject's body, notably the densities and different properties of the subject's different organs and skeleton.

Additionally, this optimization step 50 takes into account the regions of interest in the subject i.e. those regions for which precise modelling is desired, typically an internal organ or a part of the body in the case of medical imaging.

These regions of interest are either determined automatically in relation to the X-rays emitted during the first application step 10, for example by determining the intersection(s) of the X-ray beams emitted during this first application step 10, or they are designated by an operator typically on a device controlling an X-ray emitting device.

The optimization step 50 will therefore determine the directions that are best adapted to distribute the radiation dose in substantially uniform and homogeneous manner over the different regions of the subject's body, whilst obtaining precise modelling of the regions of interest.

This optimization step 50 can be used so as to automate an X-ray emission device. For the imaging of coronary arteries for example, a very few number of angles allows the system to determine a set of positions in space in which the C-arm is to be positioned so that the visual effects of projective narrowing of the arteries are minimized.

This is notably made possible with the system described in: "Computer-assisted positioning—Compas" by GE Healthcare, also described in the article "Optimizing coronary angiographic views; G Finet, J Liénard; The International Journal of Cardiac Imaging; Volume 11, Supplement 1/March, 1995").

On this principle, the computer 140 determines and displays on the screen the dose that has been reached in this set of views. It also selects a proposed view for the following angles paying heed to:

the set of angles of interest identified by Compas-type procedure, prohibiting the accumulation of a certain maximum dose on a given part of the anatomy, seeking an angle close to the current working angle.

A validation step by an operator can be added prior to each emission, so that the exposure procedure remains under the supervision of a qualified person.

It will also be noted that with the different data given to the computer 140 on the different emitted radiations, it is also possible for the computer to compute an estimate of radiation diffusions outside the patient, for example in the radiology room, and to display a depiction of this information (mapping of the room) for use by practitioners and assistants in the room.

The dose delivered to the body of the subject can be displayed either in conventional units, i.e. Gray (J/kg) or Sievert, or in an alternative way that displays the remaining duration of exposition for a given dose per time. For instance, for a defined dose rate of 50 mG·min$^{-1}$, with a threshold of 1000 mG and a dose already delivered of 500 mG, the displayed value would be (1000 mG-500 mG)/50 mG·min$^{-1}$=10 min.

If the user switches to a dose rate of 25 mG·min$^{-1}$, the displayed value will be adapted accordingly and set to 20 min.

This alternative gives practical information to the user, which can determine what duration of exposition he can use on the body of the subject without having negative consequences. This feature can also be used by the user so as to determine the dose settings that make it possible to complete the intervention without a risk of adverse side effects. Conventional units (Gray or Sievert) are indeed not convenient to manipulate, and do not provide practical information to the user.

Figure 4:
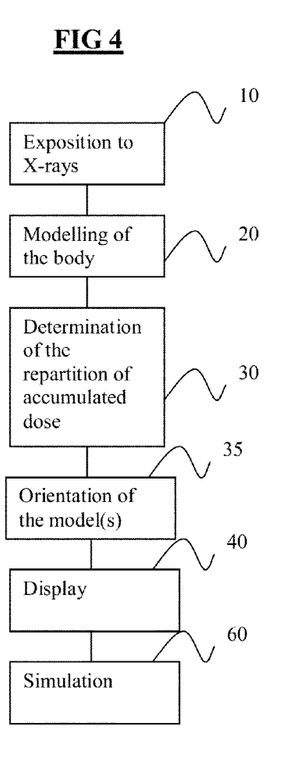

FIG. 4 illustrates another variant of the method in which the optimization step 50 is replaced by a simulation step 60 which indicates, to the operator of the device, the distribution of the X-ray dose in the body of a subject which would be obtained if the subject is subjected to exposure under given conditions, for example in a given direction.

As an example of use of this variant, the case can be cited in which, subsequent to the first three steps 10, 20 and 30, the X-ray emission system is moved by the operator of the device to orientate it in a given direction, in which case the device will indicate the consequences of such orientation in terms of exposure for the subject, or more precisely the subsequent distribution of the X-ray dose in the subject's body further to exposure in this given direction.

The user can either orientate the model in order to test various orientation using basic tools such as a 3D mouse, then once he has found an appropriate orientation, he can command the X-rays emission system in order to orientate it in a similar way as the model using secured commands, for instance with the "send angle" function.

On the contrary, the user can directly modify the orientation of the X-rays emission system using adapted commands, while the 3D model is automatically rotated accordingly for instance according to the "follow the gantry' feature.

The computer 140 can process data of a given number of expositions, i.e. duration, orientation of the emitting source 120 and properties of the body to determine the resulting dose map.

Various embodiments can therefore be conceived, for instance an embodiment where the user can perform a programming step where he programs a sequence of X-rays exposition according to various conditions prior to making any effective exposition, or after making a number of expositions and before performing another set of expositions, and then analyze the resulting dose map in the body 110 in order to determine if the expositions he defined are satisfactory both in terms of repartition of the radiation and imaging of the body 110.

Thanks to this real-time method, the user can for instance test various possible orientations of the emitting source before performing an actual X-rays emission using the orientation that provides him with the best compromise between the exposition of the body to X-rays and the resulting image of the body 110 to be imaged.

Such a compromise or trade-off can be achieved thanks to the complete set of information that is provided to the user, comprising the 3D model of the body and the dose map.

These optimization 50 and simulation 60 steps can both be implemented by a computer, which may or may not be the same as the one or those used to implement the steps of subject modelling and determination of the distribution of the X-ray dose in the subject's body.

Similarly, this computer can be combined with display means, for example allowing illustration of the directions defined under optimization, or the distribution of the X-ray dose in the subject's body under simulation, so that an operator is subsequently able to determine how to proceed with X-ray exposure of the subject.

The 3D model and the dose map can be displayed overlay on a same model or on two different models either on different frames of a same display such as a screen or on two different display devices or screens.

In the case where two different models are used, the computer 140 calculates the orientation of those models so that they are both synchronized with each other, i.e. they rotate accordingly and are displayed to the user on the same orientation which evolved according to the orientation of the emitting source 140.

FIGS. 5a, 5b, 6a and 6b illustrate respectively those two embodiments where the 3D model and the dose map are displayed overlay in a single frame of a display, or in two different frames.

In those figures, the 3D model 72 illustrated is a vessel map, while the dose map 70 is represented on an ellipsoid shape that can represent for instance the skin of the head of a subject.

Figure 5A:
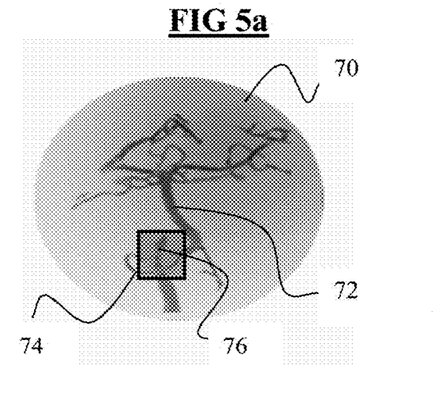
FIGS. 5a, 5b, 6a and 6b illustrate two examples of display modes of the method according to an embodiment of the invention.
Figure 5B:
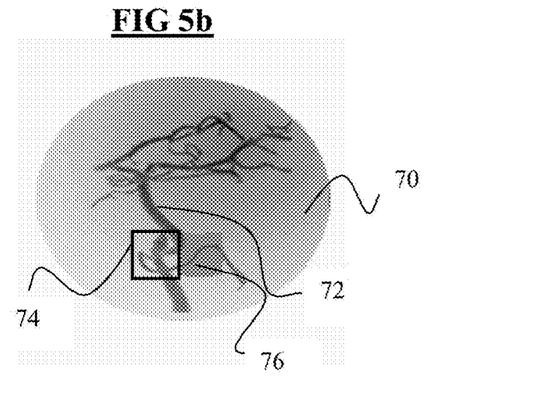

FIGS. 5a and 5b illustrate respectively a display where the dose map 70 and the 3D model are overlay at an initial state and after a change of angulations.

In those figures, the area that will be exposed to X-rays at the next exposition with the current parameters of the system is delimited by the perimeter 74, which is a square shape in this case, while the colored area 76 illustrated a zone of the skin that already received a dose of X-rays.

FIG. 5a illustrates a configuration where the perimeter 74 corresponds to the area 76, while FIG. 5b illustrated the same 3D model 72 and dose map 70 after a change of angulations.

It can be seen in FIG. 5b that the perimeter 74 is now offset relatively to the area 76. In the case of an X-rays exposition with those parameters, the user will be able to clearly identify that the area of the skin that will be exposed to X-rays is distinct from the area 76 that already received a dose of X-rays.

Figure 6A:
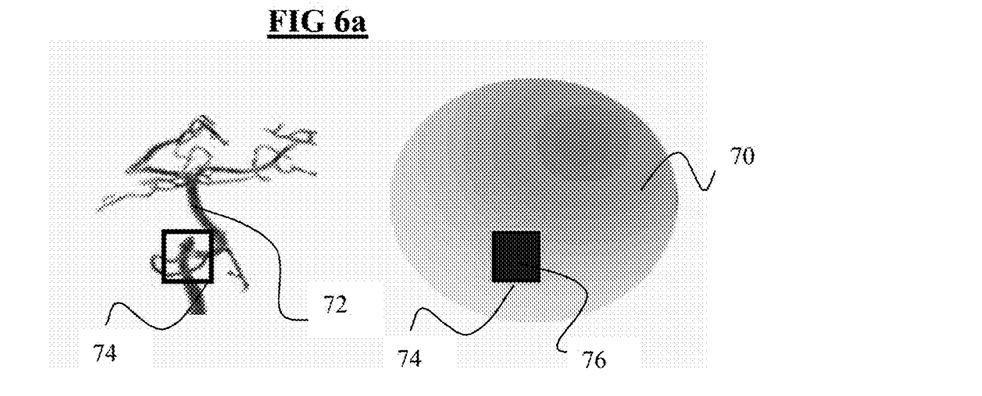
Figure 6B:
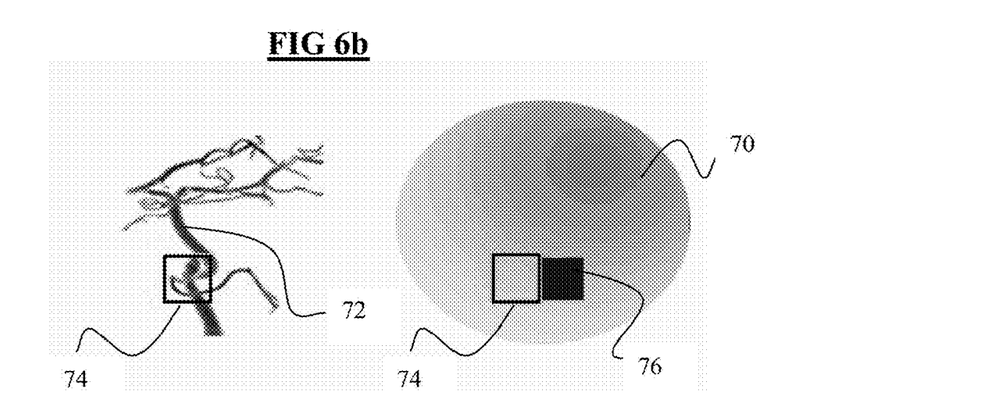

FIGS. 6a and 6b illustrate the same 3D model 72 and dose map 70 before and after a similar change of angulations.

In an alternative embodiment, the model of the body 110 to be imaged can be displayed with a semi-transparent surface so that the user can manipulate the model of the skin to adjust it in view for instance of the 3D model and the anatomical information that it provides.

Indeed, defining the location of the skin is a particularly complex step which usually leads to approximations. Therefore, allowing the user to correct the model and increase its relevance according to his or her own knowledge of the geometry of the body to be imaged can lead to improved results.

In this specific embodiment, the user can redefine the position of the skin of the model for instance by selecting a given area and repositioning it, or by repositioning a single point or a set of points while the processing unit then readjusts the model according to the new position of those points.

Figure 7A:
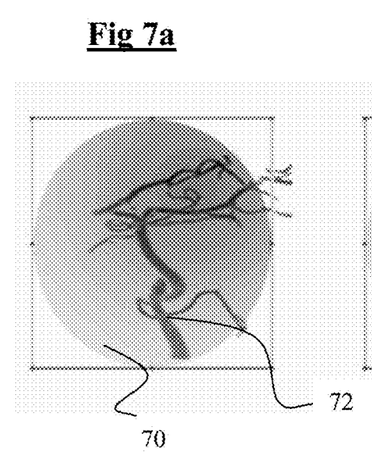
FIGS. 7a and 7b illustrate an example of adjustment of the skin model by the user according to an embodiment of the invention.
Figure 7B:
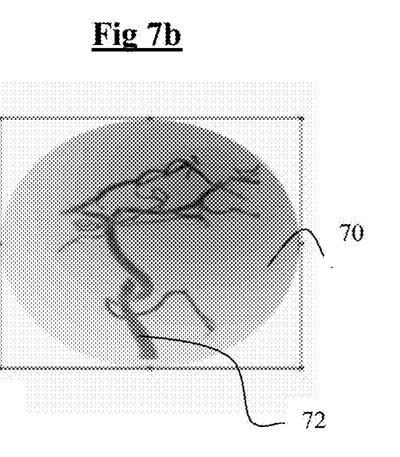

FIGS. 7a and 7b illustrate the steps of an example of manipulation of the skin model used for the dose map.

FIG. 7a illustrates an example where the 3D model 72 and the dose map 70 which used a model of the skin are obviously mismatched. Indeed, the user can see that the 3D model extends out of the dose map 70.

According to an embodiment of the invention, the user can then manipulate the model of the skin used by the dose map 70 in order to correct it, and adapt it to the 3D model 72, or more generally to the actual morphology of the subject.

This manipulation can be done using known model editing tools in order to modify the size and/or shape and/or location of the model of the skin.

This particular feature enables to improve the accuracy of the model of the skin, which is a significant improvement considering that dose mapping is based on such a model of the skin.

Conventional imaging uses standard geometrical shape depending on the protocol, which may not be adapted in all cases.

For instance, in some protocols the standard geometrical shape is an adult male, which may not be adapted for an individual of small or tall size, and could benefit highly of such an adaptation by the user.

The instructions for performing the previously detailed steps can be contained on a computer readable support comprising a computer program with code instructions adapted to implement the detailed method when said program is read by a computer, and a computer program product comprising code instructions stored on a medium able to be read by a computer such as the processing unit 5 of the imaging device 1, and comprising means capable of implementing the different steps of the method when said program is read by a computer.

What is claimed is:

1. A method for monitoring the radiation dose in a body to be imaged during interventional radiography using an X-ray imaging, device comprising an X-ray emitting source, a detector, a processing unit and a display, the method comprising:

using the X-ray emitting source to perform successive non-rotational acquisitions from different adjustable exposure angles and exposing the body to be imaged to radiation doses sufficient to acquire initial 2D images during an interventional procedure;

computing a 3D model of the body in relation to the initial 2D images using the processing unit;

computing a 3D model of a dose repartition in the 3D model of the body using a model of the interactions between matter and radiation using the processing unit;

calculating, using the processing unit, a dose map of the distribution of the accumulated radiation dose in a volume of the body for the 3D model for parameters that define the conditions of X-ray exposure;

displaying the 3D model of the body oriented according to the position of the emitting source to enable assessment of a given angulation during the interventional procedure; and simultaneously displaying the dose map in the given angulation with the 3D model, wherein the dose map comprises time values of remaining exposure time, in relation to parameters defining the conditions of X-ray exposure and a threshold value of exposure to X-rays that minimizes adverse consequences on the body.

2. The method according to claim 1, wherein the display comprises at least two frames, and wherein displaying the 3D model of the body oriented according to the position of the emitting source with the dose map comprises displaying, the 3D model of the body in one of the at least two frames of the display and displaying the dose map in another of the at least two frames of the display.

3. The method according to claim 1, wherein displaying the 3D model of the body oriented according to the position of the emitting source with the dose map comprises overlaying the 3D model of the body and the dose map in a single frame of the display.

4. The method of claim 3, comprising rotating the dose map of the accumulated radiation simultaneously with a rotation of the 3D model of the body.

5. The method according to claim 1, further comprising:
displaying the dose map on a model of the skin of the body to be imaged; and
editing the model of the skin with the processing unit based on the 3D model of the body and inputted information of relative position of the patient skin and other anatomical structures.

6. A medical imaging device comprising:
an X-ray emitting source configured to perform successive non-rotational acquisitions from different adjustable exposure angles;

a detector positioned facing the X-ray emitting source, wherein the body to be imaged is exposed to radiation doses from the X-ray emitting source to acquire initial 2D images during an interventional procedure;

a processing unit configured to:

compute a 3D model of the body in relation to the initial 2D images;

compute a 3D model of the dose reparation in the 3D model of the body using a model of the interactions between matter and radiation; and calculate a dose map of the distribution of the accumulated radiation dose in the 31) model for parameters that define the conditions of X-ray exposure; and display the 3D model of the body oriented according to the position of the emitting source which is simultaneously displayed with the dose map to enable assessment of a given angulation during the interventional procedure, wherein the dose map comprises time values of remaining exposure time, in relation to parameters defining the conditions of X-ray exposure and a threshold value of exposure to X-rays that minimizes adverse consequences on the body.

7. The medical imaging device according to claim 6, wherein the display comprises at least two frames, and wherein the 3D model of the body is displayed in one of the at least two frames of the display and the dose map is displayed in another of the at least two frames of the display.

8. The medical imaging device according to claim 6, wherein the 3D model of the body and the dose map are overlaid in a single frame of the display.

9. The medical imaging device according to claim 8, wherein the 3D model of the body and the dose map are simultaneously rotated.

* * * * *

UNITED STATES PATENT AND TRADEMARK OFFICE
CERTIFICATE OF CORRECTION

PATENT NO.       : 9,138,197 B2
APPLICATION NO.  : 13/324311
DATED            : September 22, 2015
INVENTOR(S)      : Vaillant et al.

Page 1 of 1

It is certified that error appears in the above-identified patent and that said Letters Patent is hereby corrected as shown below:

In the Specification

In Column 6, Line 67, delete "source 140." and insert -- source 120. --, therefor.

In the Claims

In Column 9, Line 12, in Claim 6, delete "31)" and insert -- 3D --, therefor.

Signed and Sealed this
Ninth Day of August, 2016

Michelle K. Lee
*Director of the United States Patent and Trademark Office*